(12) United States Patent
Messina et al.

(10) Patent No.: US 9,107,355 B2
(45) Date of Patent: Aug. 18, 2015

(54) REAL-TIME PROCESS FOR TARGETING TRAIT PHENOTYPING OF PLANT BREEDING EXPERIMENTS

(75) Inventors: Carlos Messina, Des Moines, IA (US); Jun Wei, Waukee, IA (US); Zhanshan Dong, Johnston, IA (US); Zhisheng Qing, Johnston, IA (US); Jean-Louis Laffont, Toulouse (FR); Mitchell Samples, Waukee, IA (US); Jeffrey R. Schussler, Marion, IA (US); Geoffrey I. Graham, Waukee, IA (US); Carlos Loeffler, Johnston, IA (US); Mark Cooper, Johnston, IA (US)

(73) Assignee: PIONEER HI BRED INTERNATIONAL INC, Johnston, IA (US)

( * ) Notice: Subject to any disclaimer, the term of this patent is extended or adjusted under 35 U.S.C. 154(b) by 706 days.

(21) Appl. No.: 12/763,250

(22) Filed: Apr. 20, 2010

(65) Prior Publication Data
US 2010/0286973 A1 Nov. 11, 2010

Related U.S. Application Data

(60) Provisional application No. 61/176,536, filed on May 8, 2009.

(51) Int. Cl.
| | |
|---|---|
| G01N 33/48 | (2006.01) |
| G01N 31/00 | (2006.01) |
| G06G 7/48 | (2006.01) |
| G06G 7/58 | (2006.01) |
| A01H 1/04 | (2006.01) |
| A01G 1/00 | (2006.01) |
| A01G 25/16 | (2006.01) |

(52) U.S. Cl.
CPC .. *A01H 1/04* (2013.01); *A01G 1/00* (2013.01); *A01G 25/16* (2013.01)

(58) Field of Classification Search
CPC ........... A01H 1/04; A01H 1/00; C12Q 1/6895
See application file for complete search history.

(56) References Cited

U.S. PATENT DOCUMENTS

| | | | | |
|---|---|---|---|---|
| 6,662,185 | B1 * | 12/2003 | Stark et al. ............................ | 1/1 |
| 7,378,570 | B1 * | 5/2008 | Lambeth et al. ............... | 800/267 |
| 2010/0306012 | A1 | 12/2010 | Zyskowski et al. | |

FOREIGN PATENT DOCUMENTS

WO WO2010117944 10/2010

OTHER PUBLICATIONS

Sambatti et al. "When is breeding for drought tolerance optimal if drought is random?", 2007, New Phytologist, vol. 175, pp. 70-80.*
Moreno-Gonzalez et al. "Combining genotype, environment and attribute variables in regression models for predicting the cell-means of multi-environment cultivar trials", 1998, Theoretical and Applied Genetics, vol. 96, pp. 803-811.*

* cited by examiner

Primary Examiner — Larry D Riggs, II

(57) ABSTRACT

A method for targeting trait phenotyping of a plant breeding experiment includes collecting soil data for at least one location, applying the soil data to a crop model, performing environmental monitoring at the at least one location to generate environmental data, updating the crop model with the environmental data, and using the crop model to provide predicted crop conditions. The method further includes determining environmental conditions for each of the plant breeding experiments, determining a likelihood of trait phenotype variations for each experiment using the environmental conditions and the predicted crop conditions, selecting a subset of the plant breeding experiments for collecting trait phenotype measurements based on the likelihood of trait phenotypic variation, and collecting trait phenotype measurements from the subset of the plant breeding experiments.

25 Claims, 4 Drawing Sheets

REAL-TIME PROCESS FOR TARGETING TRAIT PHENOTYPING OF PLANT BREEDING EXPERIMENTS

CROSS REFERENCE TO RELATED APPLICATIONS

This application claims the benefit of U.S. Patent Application Ser. No. 61/176,536 filed May 8, 2009, which is herein incorporated by reference in its entirety.

FIELD OF THE INVENTION

The invention relates to plant breeding. More particularly, the present invention relates to trait phenotyping within plant breeding experiments.

BACKGROUND

Accurate and precise trait phenotyping is important to the success of conventional and molecular plant breeding. As the cost of genotyping decreases it is widely understood in the scientific community that effective phenotyping is becoming the major limiting factor for implementing trait mapping, gene discovery, and molecular breeding for many plant breeding objectives. What is needed is high throughput methodologies and systems that enable real-time processes for targeting trait phenotyping within field-based plant breeding experiments.

BRIEF SUMMARY

A method for targeting trait phenotyping of a plant breeding experiment includes collecting soil data for at least one location, applying the soil data to a crop model, performing environmental monitoring at the at least one location to generate environmental data, updating the crop model with the environmental data, and using the crop model to provide predicted crop conditions. The method further includes determining environmental conditions for each of the plant breeding experiments, determining a likelihood of trait phenotype variations for each experiment using the environmental conditions and the predicted crop conditions, selecting a subset of the plant breeding experiments for collecting trait phenotype measurements based on the likelihood of trait phenotypic variation, and collecting trait phenotype measurements from the subset of the plant breeding experiments.

An apparatus includes an analysis engine, a crop model stored on a computer readable medium accessible to the analysis engine, the crop model adapted to transform data associated with plants into predictions of plant and/or crop phenotypes (i.e., plant and/or organ growth, development and/or yield and/or yield components), and a database in operative communication with the analysis engine and storing the data representative of physical conditions associated with the plants.

A system is also provided for targeting trait phenotyping of plant breeding experiments wherein the plant breeding experiments are grown at a plurality of geographically separated locations. The system includes soil sampling equipment, soil moisture monitoring equipment (manual or automatic), and manual or automated weather stations. The system further includes a central database adapted for receiving data from the soil sampling equipment, data from the soil moisture monitoring equipment, and data from the plurality of weather stations. The system also includes a crop model used for simulating environmental and phenotypic variation in target traits (i.e., growth and development of plants) within the plant breeding experiments, the crop model using the data from the soil sampling equipment, the data from the soil moisture monitoring equipment, and the data from the weather stations. The system further includes a plant sampling equipment and analysis engine to verify and correct crop model predictions in real time. The system further includes an analysis engine for applying the crop model to provide an output for targeting trait phenotyping of the plant breeding experiments.

DETAILED DESCRIPTION

Measuring trait phenotypes is important for almost every stage in the plant breeding process. Trait phenotypes include characteristics of interest including, without limitation, morphological, phenological, physiological, crop growth, genetic/genotype, and molecular traits. Although there are many possible trait phenotypes, examples of phenotypes of interest to a particular experiment may include leaf number, size, moisture, temperature, stem length and diameter, fruit size, floret initials, floret numbers, seed or fruit numbers, seed or fruit weights, carbon fractions, lipid and nitrogen concentrations in plant organs, root depth and soil occupancy, plant height, ear height, and kernel moisture content. Phenotyping is the process of collecting such data about a plant or crop. The expression of many trait phenotypes depends on the presence of appropriate environmental conditions within an experiment (e.g., water deficit conditions that impose drought stress upon plants are necessary to measure trait phenotypes that reveal genetic variation for drought tolerance). Measuring every possible trait phenotype in every experiment is impractical, particularly when the experiments are grown at multiple locations that are separated by large distances and different environmental conditions occur at the different locations. Thus, a system and a process is provided for characterizing the environmental properties of multiple experiments conducted at different locations as they emerge within a season to enable experiment managers to coordinate in real-time the effective deployment of human and equipment resources within a season to collect critical trait phenotypic data from multiple locations when the conditions within the experiments indicate a high likelihood of expressing trait genetic variation that would give rise to trait phenotypic variation.

Figure 1:
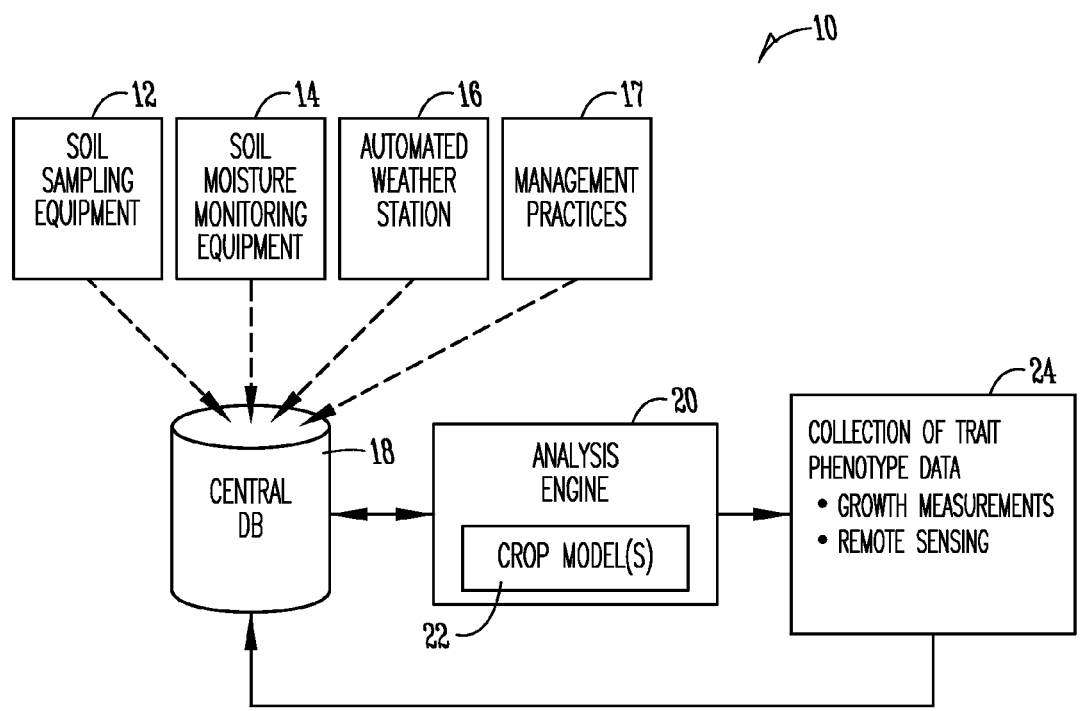
FIG. 1 is an overview of the system for targeting trait phenotyping of plant breeding experiments.

FIG. 1 provides an overview of a system 10. In the system 10, soil sampling equipment 12 is shown. The soil sampling equipment 12 is used to characterize properties of soil such as physical and chemical characteristics as well other characteristics. Soil properties may include without limitation organic matter content, moisture content, nutrient content, soil mineral composition, soil porosity, as well as other characteristics. Soil data collected using the soil sampling equipment 12 is communicated to the central database 18. Soil moisture monitoring equipment 14 and one or more automated weather station 16 are also used to collect data which may be stored in a central database 18. In addition, management practice data 17 may also be conveyed to the central database 18. The management practice data 17 may include information such as irrigation practices, seeding rates, and other types of data related to management practices. Data collected in the central database 18 is used by an analysis engine 20. The analysis engine, which may be implemented in software executing on a general purpose computer, may use a crop model 22 to assist in analysis. Numerous examples of crop models exist. These include: Simple and Universal CROp growth Simulator (SU-CROS), an open source crop growth model; Genotype-by-Environment interaction on CROp growth Simulator (GE-CROS); ORYZA2000, a rice growth model; Crop Environment Resource Synthesis (CERES) model; SORKAM, a grain sorghum crop growth model; CropSyst; and SWACROP models. Of course other crop models may be used. The selection of a particular crop model to use may be based, at least in part, on the type of crop being modeled or the available data, or other factors.

The analysis engine 20 may be used to assist in the collection of trait phenotype data 24. This may include specifying at which field experiments data should be collected and at what time the data should be collected. Thus, by using the crop model 22 to provide predicted crop conditions, the analysis engine can reduce the amount of resources that must be allocated for data collection and/or increase the likelihood that collection of trait phenotype data is collected at a correct time. The analysis engine 20 as shown is implemented on a computer or other computing device. For example, the analysis engine 20 may be implemented in software stored on a computer readable medium.

Any number of trait phenotype measurements may be collected. It is to be understood that trait phenotypes include characteristics of interest including morphological, phenological, physiological, genetic/genotype, crop growth, and molecular traits. Phenotyping is the process of collecting such data about a plant or crop. The particular trait phenotype data collected is determined by type of crop. In addition, different types of phenotype data may be collected as a matter of plant breeder preference.

Examples of phenotype traits which can be measured either quantitatively or qualitatively for corn include, without limitation, yield, stalk strength, root strength, grain quality, stress resistance, insect resistance, physiological plant characteristics (including seed dry down, standability, nutrient utilization, and male sterility). Of course, many different phenotypic traits are of potential interest depending on the type of plant and the desired qualities of the plant.

Figure 2:
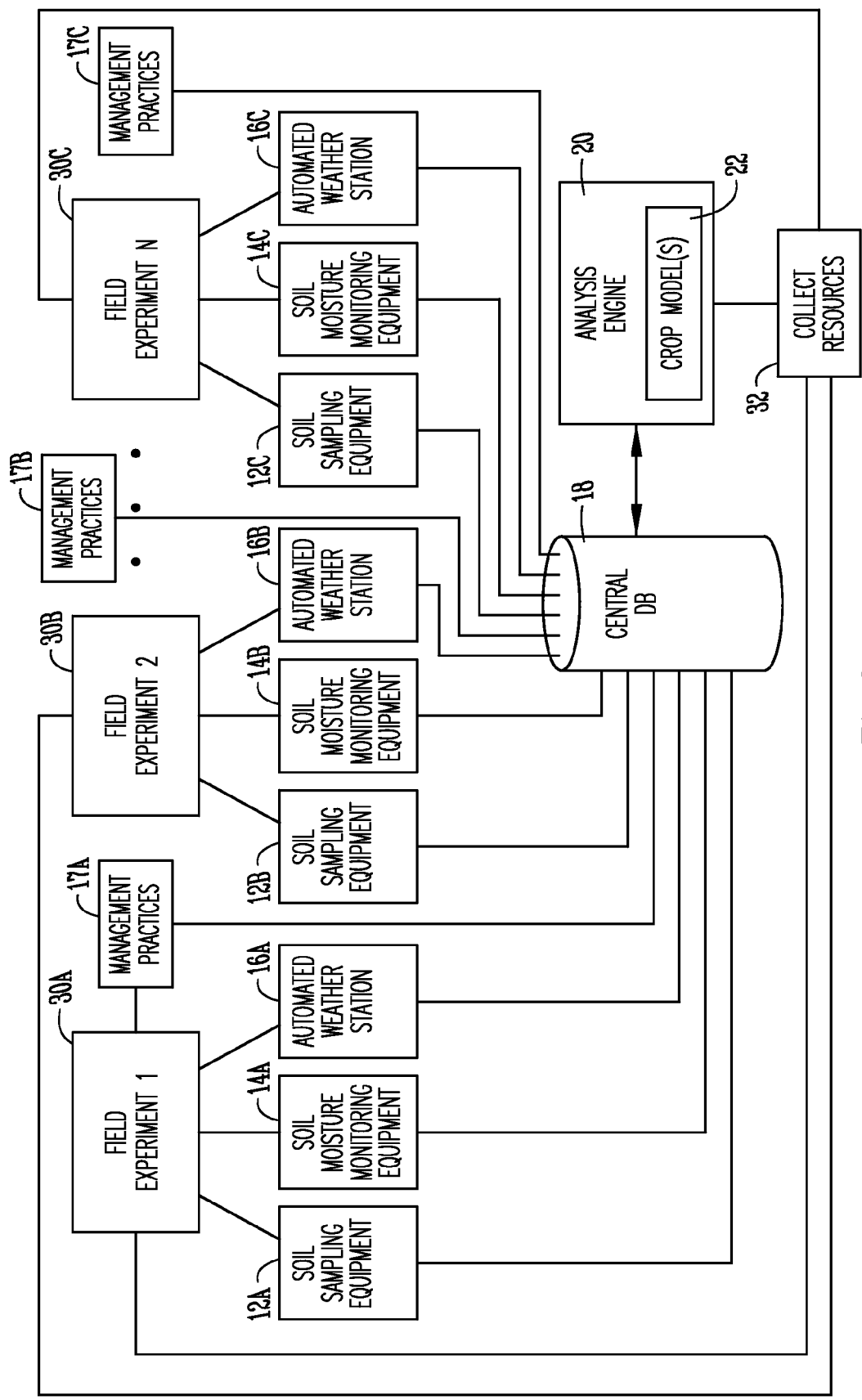
FIG. 2 is another diagram of the system for targeting trait phenotyping of plant breeding experiments.

By way of further example, FIG. 2 illustrates multiple field experiments 30A, 30B, 30C. Note there may be any number of field experiments and the field experiments may be spread across geographically diverse locations. There are soil sampling equipment 12A, soil moisture monitoring equipment 14A, and an automated weather station 16A associated with the field experiment 30A. In addition, management practices data 17A associated with the field experiment 30A may be collected. There are soil sampling equipment 12B, soil moisture monitoring equipment 14B, and an automated weather station 16B associated with the field experiment 30B. In addition, management practices data 17B associated with the field experiment 30BA may be collected. There are soil sampling equipment 12C, soil moisture monitoring equipment 14C, and an automated weather station 16C associated with the field experiment 30C. In addition, management practices data 17C associated with the field experiment 30C may be collected. Data from the soil sampling equipment 12A, 12B, 12C, the soil moisture monitoring equipment 14A, 14B, 14C, the automated weather stations 16A, 16B, 16C, and the management practices data 17A, 17B, 17C, are collected into a central database 18 which is accessed by the analysis engine 20. The analysis engine 20 is used to allocate collection resources 32 associated with the collection of trait phenotype data. Collection resources 32 may be allocated to particular field experiments at particular times based on the results from the analysis engine 20.

Thus, environment monitoring equipment may be deployed to one or more locations associated with field experiments. The environment monitoring equipment may include soil sampling equipment to characterize standard soil physical and chemical properties, soil moisture monitoring equipment to provide real-time measurements of soil moisture status, and automated real-time weather stations to measure temperature, rainfall, wind-run, and incident radiation. The data may then be organized for automated transfer to a centralized location for analysis, such as central database 18.

From the beginning of the crop season the data are used as input variable to run an appropriate crop model, such as a crop growth model, on a continual basis. The model may be used to predict crop growth and development for the whole season based on historical data collected from the same location in previous years supplemented with current season data as it is downloaded. Historic data may also be stored in the central database 18 or is otherwise accessible by the analysis engine 20. Such an approach allows on a daily basis (or more frequently) real-time predictions of the crop conditions for each experiment.

The ongoing crop growth and development predictions from the real-time model runs may be used as predictors of the environmental conditions encountered within each experiment. Thus, the impact of the environmental conditions may be determined.

The predicted environmental conditions combined with the predicted crop growth and development patterns within each experiment may be used to predict the likelihood of relevant trait phenotypic variation for each experiment using statistical methods such as partial least squares regression analysis. Of course, other statistical methods may be used including other types of multivariate analysis. Other types of analysis may include canonical correlations, neural networks, mixed model frameworks, principal components analysis, eigenvector-based analysis, correspondence analysis, and K-means clustering.

The prediction of the likelihood of relevant trait variation for each experiment may be used to deploy human and equipment resources to experimental locations to collect relevant trait phenotype measurements (or data). For example, plant growth and/or ear growth measurements may be used to determine the impact of drought stress on phenotypic variation. Remote sensing, such as aerial-based remote sensing measurements, may be appropriately timed to critical stages of crop growth and development. Also plant height and/or ear height measurements may be performed at locations where maximum variation is predicted to be expressed. Alternatively, other measurements associated with physiological or morphological plant traits may be made.

The particular physiological or morphological plant traits of interest will vary depending on the type of plant and which traits are of interest in a particular breeding program.

The resulting system and process allows for efficient deployment of available human and equipment resources to multiple remote locations to obtain critical trait phenotype measurements from relevant locations even when it is not feasible to measure all trait phenotypes at all locations.

Figure 3:
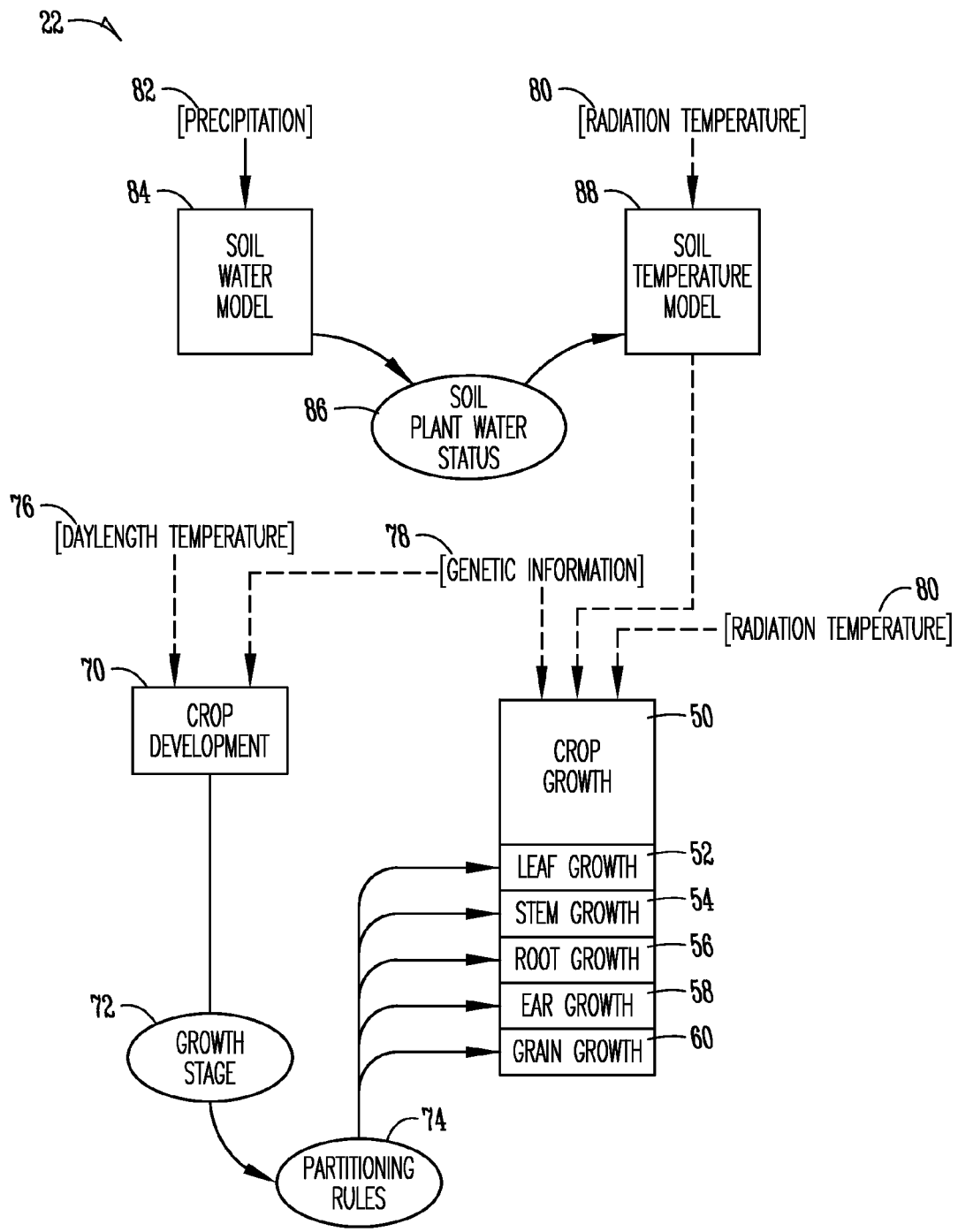
FIG. 3 is a diagram of one example of a crop model which may be used in a system for targeting trait phenotyping of plant breeding experiments.

FIG. 3 illustrates a simplified crop model 22. The crop model 22 may include a number of different models. For example, a crop growth processes model 50 is shown for modeling leaf growth 52, stem growth 54, root growth 56, ear growth 58, and grain growth 60. A crop growth model may be used to determine a crop's response to its developmental environment.

A crop development model 70 is shown. The crop development model 70 may be used to track the progression of the crop through various phenological stages and allow specific phenological conditions to be matched with particular environmental conditions. For example, silking or an interval of time around silking may be matched to one or more of a given soil moisture content, air/leaf temperature, or solar radiation. In addition the overall crop model 22 as shown also includes a soil water model 84 and a soil temperature model 88. Of course, any number of other models may be included in the overall model, including the models for nitrogen availability, plant nitrogen utilization, and others.

The crop model 22 has various inputs. As shown in FIG. 3, data inputs such as precipitation 82 and radiation temperature 80 are used. In addition, information such as genetic information 78 may also be used. The crop model comprises a large input set of parameters for genotype information denoted as genetic coefficients. Genetic coefficients include but are not limited to genotype, pedigree information, marker information, QTLs, haplotype information, or transgene information. In some examples, the crop model may use specific set of parameters to characterize different varieties or hybrids. In some examples the specific set of parameters is a subset of a larger set of parameters, or related to a specific crop variety or strain, or related to a specific experimental design, or selected based on any other criteria, or a combination thereof. Sometimes the crop model may include genetic coefficients as parameters. Thus, plant genotype may be taken into account by the crop model. Model completeness and complexity can vary significantly and it is contemplated that any number of models may be used. Thus, various models may use more or less data than other models.

Examples of weather data which may be used in a particular model includes incoming solar radiation, maximum air temperature, minimum air temperature, precipitation, humidity, and wind speed. Examples of soil input data which may be used includes albedo, upper flux limit, drainage coefficient, runoff curve number, and soil layer data. The soil layer data may include lower soil water content limit for plant growth, drained upper soil water content limit, field-saturated soil water content, relative distribution for root growth, and hydraulic conductivity. In addition, the soil input data may include physical and chemical characteristics of the soil. The physical and chemical characteristics of the soil may be used to make estimates for some of the other soil data.

Figure 4:
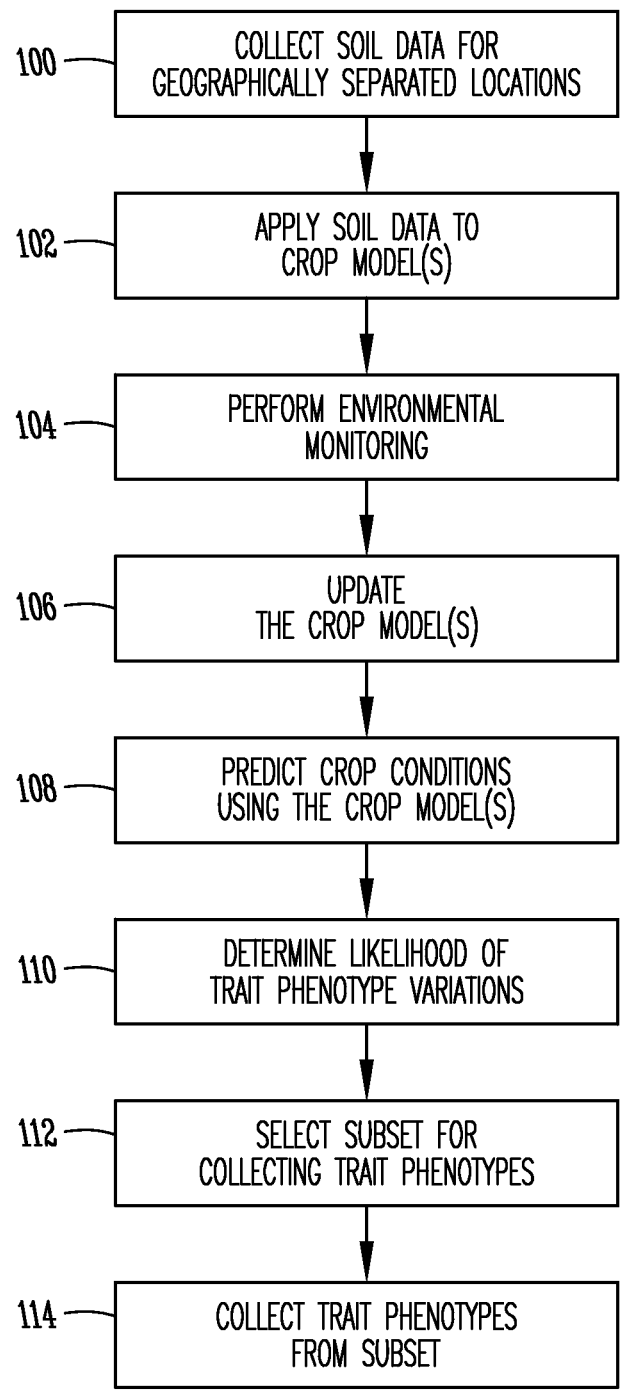
FIG. 4 is a flow chart illustrating a process for collecting trait phenotypes from plant breeding experiments.

FIG. 4 illustrates one example of a method. In step 100 soil data are collected for geographically separated locations, such as for different field experiments. In step 102 the collected soil data are applied to one or more crop models. In step 104 environmental monitoring is performed at the geographically separated locations, such as different field experiments. In step 106, the crop model or models are updated. In step 108, crop conditions are predicted using the crop model or models. In step 110, a likelihood of trait phenotype variations may be calculated for each location or field experiment. In step 112, a subset of locations or field experiments may be selected for collecting trait phenotype measurements. In step 114, trait phenotype measurements from the subset of locations or field experiments may be collected. The trait phenotypes may be collected in various ways, including by hand, by machine, through the use of remote sensing, including aerial or satellite-based remote sensing. It is to be understood, although the steps are shown in a linear manner, the steps need not be executed linearly. For example, the environmental monitoring may periodically or continuously update the crop model or models. Thus predictions of crop conditions may also be periodically or continuously updated.

One out of the many possible implementations of the method for targeting trait phenotyping of plant breeding experiments was used in 2008. This implementation included collecting soil data from existing surveys for five geographically separated locations in the Midwest, applying the soil data to a crop model, performing environmental monitoring at the geographically separated locations using a set of automatic weather stations and soil moisture metering devices to generate environmental data, updating the crop model with the environmental data at recurrent times during the growth cycle, using the crop model to provide predicted crop conditions, and determining environmental conditions for each of the plant breeding experiments. Predicted crop and soil water conditions were used for several different real-time decisions at the locations: whether to irrigate at one location; to select one out of the five locations to screen breeding populations for plant water status; to select one out of the five locations to screen breeding populations for canopy traits; and to select two out of the five locations to phenotype selected hybrids for phenology, plant height, crop growth, temporal changes in canopy traits, yield and yield components. Using the methods to decide when or whether to irrigate was a key decision for collecting real-time and cumulative data on drought stress and expose genetic variation for complex traits underpinning drought tolerance in the selected experiments. Another application was to predict genetic variation for plant height. Predictions were generated for all research field evaluation sites and plant and ear height measures were taken only in those sites with above average predicted genetic variance for those traits.

In 2009, an implementation similar to the one described for 2008 was also carried out at five locations. Additionally, predicted crop and soil water conditions were used for real-time irrigation decisions at 30 other locations. This improved the rate of success at generating environments for drought phenotyping as compared with previous years, when more subjective methods were used. Also in 2009, real time simulations were used to predict genetic variation for plant height at 1434 locations. Of this total, 425 were chosen for plant height phenotyping based on their high predicted genetic variance. This allowed restricting the sampling of environments to those that maximized the expression of genetic differences for this trait and hence improved the genetic gain achieved by unit of phenotyping phenotyping resources invested.

Therefore, methods, apparatus and systems for targeting trait phenotyping in plant breeding experiments have been disclosed. Numerous variations, alternatives, and options are contemplated. These include variations in the type of crop, variations in the crop models used, variations in the data collected, variations in the resources which are used for collecting phenotypes, and other variations.

What is claimed is:

1. A method for targeting trait phenotyping of multiple plant breeding experiment, the method comprising:
   collecting soil data for at least one location;
   applying the soil data to a crop model;
   performing environmental monitoring at the at least one location to generate environmental data;
   updating the crop model with the environmental data;

using via a computer an analysis engine comprising the crop model to provide predicted crop conditions;

determining environmental conditions for each of the plant breeding experiment;

determining a likelihood of trait phenotype variations for each experiment using the environmental conditions and the predicted crop conditions;

selecting a subset of the plant breeding experiments for collecting trait phenotype measurements, the selected subset of the plant breeding experiments having an above average predicted trait phenotypic variation within a season; and collecting trait phenotype measurements from the subset of the plant breeding experiments within the season.

2. The method of claim 1 wherein the at least one location is a plurality of geographically separated locations.

3. The method of claim 1 further comprising determining at least one management practices at the at least one location.

4. The method of claim 1 wherein the step of determining the likelihood of trait phenotypic variations being performed with statistical methods.

5. The method of claim 4 wherein the statistical methods include partial least squares regression analysis.

6. The method of claim 1 wherein the trait phenotype measurements include plant measurements.

7. The method of claim 6 wherein the plant measurements include one or more plant measurements from the set consisting of leaf number, size, moisture, temperature, stem length and diameter, fruit size, floret initials, floret numbers, seed or fruit numbers, seed or fruit weights, carbon fractions, lipid or nitrogen concentrations in plant organs, root depth and soil occupancy, plant height, ear height, and kernel moisture content.

8. The method of claim 6 further comprising evaluating the physiological or morphological plant measurements to assist in determining impact of environments on phenotypic variation.

9. The method of claim 1 wherein the subset of the collecting of trait measurements is performed using remote sensing.

10. The method of claim 9 wherein the remote sensing is aerial remote sensing.

11. The method of claim 1 wherein the subset of the plant breeding experiments is selected based on likelihood of expressing maximum variation for the trait phenotypes.

12. The method of claim 11 wherein the trait phenotypes include physiological or morphological plant traits.

13. The method of claim 1 wherein the crop model simulates crop growth and crop development.

14. An apparatus, comprising:
a computer configured to execute an analysis engine;
a crop model stored on a computer readable medium accessible to the analysis engine, wherein the crop model is adapted to transform environmental data at least one location into predictions of plant growth or development of plants at the at least on location; and,
a database in operative communication with the analysis engine, wherein the database comprises stored and real-time data which includes at least one physical condition of the plants at the at least one location within a season;
wherein the analysis engine produces output used to determine a likelihood of trait phenotype variation within the season and to select a subset of plant breeding experiments for collecting trait phenotype measurements, the selected subset of the plant breeding experiments having an above average predicted trait phenotypic variation within the season, and
wherein trait phenotype measurements are collected from the subset of the plant breeding experiments within the season.

15. The apparatus of claim 14 wherein the environmental data comprises soil data at the at least one location.

16. The apparatus of claim 14 wherein the environmental data comprises weather data at the at least one location.

17. A system for targeting trait phenotyping of a plant breeding experiment, the system comprising:
soil sampling equipment;
soil moisture monitoring equipment;
one or more weather stations;
a central database adapted for receiving data from the soil sampling equipment, data from the soil moisture monitoring equipment, and data from the one or more weather stations;
a crop model using the data from the soil sampling equipment, the data from the soil moisture monitoring equipment, and the data from the one or more weather stations; and
a computer configured to execute an analysis engine for applying the crop model to provide an output for targeting a trait phenotyping of the plant breeding experiments,
wherein the output is used to determine a likelihood of train phenotype variation within a season and to select a subset of the plant breeding experiments of collecting trait phenotype measurements, the selected subset of the plant breeding experiments having an above average predicted trait phenotypic variation within the season, and
wherein trait phenotype measurements are collected from the subset of the plant breeding experiments within the season.

18. The system of claim 17 wherein the analysis engine applies statistical methods to assist in providing the output.

19. The system of claim 17 wherein the output is used to determine timing or location of trait phenotype data.

20. The system of claim 17 wherein the output being environmental characteristics of testing locations.

21. The system of claim 17 wherein the output being associated with locations with maximum variation for the trait phenotypes.

22. The method of claim 1, further comprising updating the crop model based on the trait phenotype measurements collected from the subset of plant breeding experiments.

23. The method of claim 1, wherein the environmental condition is drought.

24. The method of claim 3, wherein at least one management practice is irrigation.

25. The method of claim 1, wherein the likelihood of trait phenotype variation is determined for plant height.

* * * * *